United States Patent [19]

Boney

[11] 4,195,191

[45] Mar. 25, 1980

[54] NON-REGENERATIVE HF ALKYLATION PROCESS

[75] Inventor: William G. Boney, Rolling Meadows, Ill.

[73] Assignee: UOP Inc., Des Plaines, Ill.

[21] Appl. No.: 670,491

[22] Filed: Mar. 25, 1976

Related U.S. Application Data

[63] Continuation-in-part of Ser. No. 562,699, Mar. 27, 1975, abandoned, which is a continuation-in-part of Ser. No. 360,258, May 14, 1973, abandoned.

[51] Int. Cl.² .............................................. C07C 3/54
[52] U.S. Cl. .................................. 585/706; 585/719; 585/723
[58] Field of Search ...................... 260/683.48, 683.49, 260/683.51

[56] References Cited

U.S. PATENT DOCUMENTS

| | | | |
|---|---|---|---|
| 2,322,800 | 6/1943 | Frey | 260/683.48 |
| 2,394,906 | 2/1946 | Frey | 260/683.48 |
| 2,990,437 | 6/1961 | Berger | 260/683.48 |
| 3,073,877 | 1/1963 | Sherk | 260/683.48 |
| 3,763,265 | 10/1973 | Hutson, Jr. et al. | 260/683.48 |

Primary Examiner—George Crasanakis
Attorney, Agent, or Firm—James R. Hoatson, Jr.; Robert W. Erickson; William H. Page, II

[57] ABSTRACT

An improved isoparaffin/olefin HF alkylation process designed to function absent the commonly-utilized acid regenerator. Polymer products, formed during the alkylation reaction, are recovered with the normally liquid alkylate product, substantially free from HF, without effecting degradation in the product quality. In addition to enhanced economic considerations stemming from a reduction in equipment costs, the operational stability of the process is significantly improved.

8 Claims, 2 Drawing Figures

NON-REGENERATIVE HF ALKYLATION PROCESS

RELATED APPLICATIONS

The present application is a Continuation-In-Part of my copending application Ser. No. 562,699, filed Mar. 27, 1975, now abandoned, which, in turn, is a Continuation-In-Part of copending application Ser. No. 360,258, filed May 14, 1973, now abandoned, all the teachings of which copending applications are incorporated herein by specific reference thereto.

APPLICABILITY OF INVENTION

The invention herein described is intended for utilization in the production of a normally liquid alkylate product via the reaction of an isoparaffin with an olefin, or olefin-acting compound. Although intended for use in improving any well-known acid-catalyzed alkylation process—e.g. sulfuric acid alkylation—my invention is most applicable with respect to those processes which are effected in contact with a hydrogen fluoride catalyst. More than 33 years ago, the demand for high-octane fuels, possessing enhanced anti-knock properties, increased at a staggering rate. These improved fuels were required in voluminous quantities to satisfy the then-accelerating degree of consumption. Within the petroleum industry, various processes were developed which proved successful in alleviating the intertwined problems attendant supply, quality and demand. Among the first of such processes was the acid-catalyzed alkylation of an isoparaffin with an olefin, both generally normally vaporous, to produce a higher molecular weight, normally liquid isoparaffin. Since isoparaffins, as contrasted to normal paraffins, possess significantly higher octane ratings and blending values, and thus greatly improve anti-knock properties, processes capable of efficiently effecting such a reaction have gained, and continue to gain wide acceptance within the petroleum industry.

For many economic and technical reasons, well known to those having the requisite skill in the appropriate art, the alkylation process catalyzed through the use of hydrogen fluoride predominates overwhelmingly. HF alkylation of an iosparaffin with an olefin has, since the advent thereof, experienced a multitude of changes and improvements with respect to unit design and operating techniques. My invention also constitutes a design renovation which results in significant improvement in operational stability, while simultaneously affording economic advantages, by providing a non acid-regenerative alkylation process.

OBJECTS AND EMBODIMENTS

A principal object of the present invention is to effect an improvement in the hydrogen fluoride alkylation of hydrocarbons. A corollary objective is to enhance the economics attendant the alkylation of a normally vaporous isoparaffin with a normally vaporous olefinic hydrocarbon to produce a normally liquid alkylation product.

A specific object of my invention involves the elimination of the acid regenerator in a hydrogen fluoride alkylation process.

Another object of the present invention is directed toward the acid-catalyzed alkylation of lower-boiling isoparaffins, such as isobutane, with olefinic hydrocarbons such as, for example, propylene, the butylenes, various amylenes and mixtures thereof.

Therefore, in one embodiment, my inventive concept encompasses a process for the non acid-regenerative alkylation of an isoparaffin with an olefin, to produce a normally liquid alkylate product, which process comprises the steps of: (a) reacting said isoparaffin with said olefin, in admixture with a hydrogen fluoride catalyst, in an alkylation reaction zone, at alkylating conditions resulting in a reaction product effluent containing (i) normally liquid alkylate, (ii) unreacted isoparaffin, (iii) hydrogen fluoride catalyst and, (iv) polymer products; (b) introducing said reaction product effluent into a separation zone and recovering therefrom (i) a hydrocarbon phase and, (ii) a hydrogen fluoride phase containing said polymer products; (c) recycling a first portion of said hydrogen fluoride phase to said reaction zone for contact therein with said isoparaffin and olefin; (d) heating said hydrocarbon phase to a temperature greater than the temperature of said reaction product effluent, and in the range of about 125° F. to about 200° F., to increase the solubility potential of hydrogen fluoride therein: (e) commingling a second unheated portion of the hydrogen fluoride phase with the heated hydrocarbon phase, in an amount soluble in said hydrocarbon phase; and (f) countercurrently stripping the resulting mixture, in a stripping zone, with an isoparaffin-containing stream and separately removing therefrom (i) unreacted isoparaffin and, (ii) said normally liquid alkylate product, containing polymer products.

Other objects and embodiments will become apparent from the following additional description of the present inventive concept and the process encompassed thereby, as well as from the description of the accompanying drawings.

PRIOR ART

Candor compels recognition and acknowledgment of the fact that the prior art is replete with a wide variety of publications, inclusive of issued patents, directed toward the acid-catalyzed alkylation of an isoparaffin with an olefin. This is particularly true with respect to hydrogen fluoride alkylation which traces its development over an approximate 30-year period. Any attempt herein to exhaustively delineate the hydrogen fluoride alkylation art would constitute an exercise in futility. However, it is believed that a brief description of the more recent innovations, for the purpose of illustrating the utilization of the present improvement, will serve to define the area to which the technique of the present invention is particularly applicable.

U.S. Pat. No. 3,560,587 (Cl. 260-683.48) describes the hydrogen fluoride alkylation of an isoparaffin/olefin mixture in a system incorporating a reaction cooler, reaction soaker and a hydrogen fluoride acid-settler. The greater proportion of the hydrogen fluoride phase, separated in the settler, is recycled to the cooled reaction zone for further contact with the reactant mixture. The remaining portion is indicated as being transferred to suitable acid regeneration facilities for the separation therein of polymer products.

U.S. Pat. No. 3,686,354 (Cl. 260-683.43) is fairly illustrative of a complete hydrogen fluoride alkylation system including reaction vessels, reaction effluent separation for acid recovery and product separation for the recovery of the normally liquid alkylate product. In this system, the alkylate product is separated into a relatively high-octane fraction and relatively low-octane fraction, the latter being further treated with additional isoparaffin and hydrogen fluoride catalyst. An integral part of the process as illustrated involves introducing at least a portion of the recovered hydrogen fluoride catalyst into a suitable regeneration system for the purpose of removing polymer products formed during the reaction. U.S. Pat. No. 3,713,615 (Cl. 196-102) is specifically directed toward a fractionation vessel for utilization in the separation of the product effluent from the alkylation reaction zone. It is contemplated therein that at least a portion of the recovered hydrogen fluoride catalyst will be subjected to regeneration in order to separate the polymer products.

U.S. Pat. No. 3,249,650 (Cl. 260-683.48) offers another fairly complete illustration of a hydrogen fluoride alkylation process in which a portion of the separated catalyst is regenerated to recover polymer products; in this instance, the polymer products are utilized in supplying a portion of the required heat energy of the process.

Although the foregoing illustrations are directed to different innovations, they do possess a common integrated technique. That is, the regeneration of at least a portion of the separated hydrogen fluoride catalyst for the purpose of removing polymer products formed during the reaction of the isoparaffin/olefin reactant stream. Historically, polymer products have been periodically removed from an HF alkylation reaction system in order to prevent the accumulation thereof to the extent that reaction stability, catalyst activity and efficiency are significantly impaired. Furthermore, it has been believed that such polymer products could not be recovered as a portion of the desired product effluent due to their propensity for effecting degradation of the alkylate product. This particular prior art technique possesses several disadvantages which the present invention readily overcomes. In a hydrogen fluoride alkylation process, polymer products are formed at a rate approximating 10 to about 20 Bbl./day for a unit designed for a charge capacity of about 10,000 Bbl./day. Therefore, in the prior art processes, the acid regenerator is placed in on-stream service approximately one day out of every seven to about ten days. Units which are "pushed" beyond the intended design capacity will generally regenerate the acid stream more frequently—about two to six days—or continuously, depending upon the degree to which over-capacity is practiced. This type of sporadic operation inherently results in temporary, but significant upsets regarding operational stability. Furthermore, such prior art designs require the installation of a relatively expensive piece of equipment which is not in constant use.

The technique encompassed by my inventive concept eliminates the acid regenerator from the system, and recovers the polymer products, formed during the alkylation reaction, with the normally liquid alkylate product without effecting a degradation in the quality thereof, simultaneously eliminating upsets in operating stability stemming from the periodic placement of an acid regenerator on-stream. Additionally, the liquid alkylate product is recovered substantially free from hydrogen fluoride. Simultaneously, the unreacted isoparaffin and HF-acid mixture is recovered, for ultimate recycle to the reaction zone, substantially free from foreign matter including acid sulfur oils, polymer products, etc. That is, the principal difficulty attendant the separation of the reaction product effluent, following recycle of the settled HF-acid and in the absence of the acid regenerator, resides in separating the HF-acid from the foreign matter. It has been shown, through the use of my inventive concept, that recovery of foreign matter in the alkylate product effluent has no detrimental effect respecting product quality, either as to octane rating, or color. In this regard, where substantial quantities of HF-acid appear in the alkylate product, degradation thereof is experienced.

I have now determined that this perplexing difficulty is readily solved by controlling the feed mixture to the isostripping column. Briefly, where the quantity of the acid phase, not recycled to the reaction zone, contains an amount of HF-acid, required to remove the foreign matter from the system, which is greater than the solubility of acid in the hydrocarbon phase, then HF-acid will appear in the liquid alkylate product withdrawn as a bottoms stream from the isostripping column. There are several techniques which can be employed to insure that the alkylate product is recovered substantially free from HF-acid, while simultaneously removing a sufficient quantity of foreign matter to prevent the deleterious buildup thereof in the reaction section. For example, the recycle of unreacted isoparaffin to the reaction zone can be adjusted to increase the quantity of acid soluble in the isostripper overhead stream.

However, the preferred, simplified technique involves raising the temperature of the hydrocarbon phase recovered from the settling zone to a level greater than that of the total reaction zone effluent. That portion of the settled HF-acid phase not being recycled to the reaction zone, and which would otherwise have been introduced into the acid regenerator, is not so heated, but immediately admixed with the thus-heated hydrocarbon phase and introduced therewith into the isostripping column. The temperature of the hydrocarbon phase is raised to a level generally in the range of about 125° F. to about 200° F. An isoparaffin stripping medium countercurrently contacts the isostripper feed stream and effectively removes HF-acid in the overhead stream.

U.S. Pat. No. 3,579,603 (Cl. 260-683.48) primarily directs itself to a novel alkylation-fractionator apparatus (and process using the same) having a built-in acid settling vessel. All "products" of the process are separately withdrawn from this single vessel. These include: vent gas; propane; isobutane, for recycle to the isobutane/olefin feed mixture; settled HF acid, for recycle to the alkylation reaction vessel; normal butanes; and, the normally liquid alkylate product. Although not illustrated in the accompanying drawing, it is stated that a portion of the recycled HF acid may be diverted to an acid regenerator. Furthermore, there is no external separation of the reaction product effluent accompanied by raising the temperature of the hydrocarbon phase, to increase the solubility potential of HF acid therein, prior to the introduction thereof into the alkylation-fractionator.

A combination alkylation/isomerization process is disclosed and described in U.S. Pat. No. 2,394,906 (Cl. 260-683.48). HF acid from the acid settler is in part recycled to the alkylation reaction zone, the remainder being utilized as catalyst for the conversion of normal butane to isobutane, the latter being part of the hydrocarbon feed to the alkylation zone. The hydrocarbon phase from the settler is introduced into a fractionator from which motor fuel alkylate and polymer products are separately recovered. With respect to the present application, the reference fails to recognize (1) increasing the temperature of the hydrocarbon phase introduced into the fractionator and, (2) commingling an unheated portion of the settled HF acid therewith. Also, as above stated, the polymer products are recovered as a bottoms stream separate from the motor fuel alkylate product.

U.S. Pat. No. 2,322,800 (Cl. 260-283.48) involves a technique wherein portions of the olefinic feed stream are introduced at various loci of the reaction zone. Since this avoids a relatively high olefin concentration at any given point in the reaction vessel, it is alleged that polymer product formation is inhibited. Contrary to the present technique, there is no initial separation of the reaction zone effluent into a hydrocarbon phase and an HF-acid phase. That is, the effluent is directly recycled in part to the reaction zone with the remainder being directly introduced into the fractionator. Since the effluent is not initially separated, there exists no separate heating of the hydrocarbon phase followed by the addition thereto of a portion of unheated HF-acid phase.

In U.S. Pat. No. 2,372,338 (Cl. 260-283,41), the reaction product effluent is introduced into a settling zone from which a hydrocarbon phase and an HF-acid phase are recovered. As in the present process, the greater portion of the HF-acid phase is recycled to the reaction zone. Of the remainder, a first portion is withdrawn from the system and introduced into an external acid regenerating zone, while a second portion is increased in temperature and admixed with the hydrocarbon phase, none of which is subject to preheating. The mixture is then introduced into a fractional distillation column which employs a high external reflux ratio. The described process is, quite clearly, in contradistinction to that encompassed by my inventive concept. As disclosed, following the phase separation via settling, only a portion of the HF-acid phase is heated and combined with unheated separated hydrocarbons for introduction into the fractionator. As an alternative, not all of the HF-acid phase is heated. There exists, therefore, no recognition of increasing the solubility potential of HF-acid in a heated hydrocarbon phase.

SUMMARY OF INVENTION

As hereinabove set forth, my invention is directed toward an improvement in a process for alkylating an isoparaffin/olefin reactant stream. Although particularly applicable to the alkylation of isobutane with a butylene-containing olefinic stream, the process is also adaptable for utilization with other isoparaffinic and olefinic feed stocks for the purpose of producing motor fuel or aviation alkylates. Suitable isoparaffinic hydrocarbons are those having from about 4 to about 7 carbon atoms per molecule, including isobutane, isopentane, neopentane, one or more of the isohexanes and various branched-chain heptanes. Similarly, the olefinic reactant contains from about 3 to about 7 carbon atoms per molecule, and includes propylene, 1-butene, 2-butene, isobutylene, the isomeric amylenes, hexenes, and various heptenes.

The alkylation reaction mixture comprises hydrogen fluoride catalyst, an isoparaffin and an olefinic hydrocarbon; hydrogen fluoride is utilized in an amount generally sufficient to provide a catalyst/hydrocarbon volume ratio within the reaction zone of from about 0.5 to about 3.0. Hydrogen fluoride, as employed throughout the present specification and appended claims, is intended to include catalysts where hydrogen fluoride is the essential active ingredient. It is, therefore, within the scope of the present invention to employ substantially anhydrous hydrogen fluoride, hydrofluoric acid, or hydrogen fluoride containing various additives or promoters. As a general practice, commercial anhydrous hydrogen fluoride will be charged to the alkylation system as fresh catalyst. It is possible to use hydrogen fluoride containing as much as about 10.0% water; however, excessive dilution with water is undesirable since it tends to reduce the alkylating activity of the catalyst and introduces severe corrosion problems into the system. In order to reduce the tendency of the olefinic portion of the hydrocarbon feed stock to undergo polymerization prior to alkylation, the molar proportion of isoparaffin to olefinic hydrocarbon within the alkylation reaction zone is maintained at a value greater than about 1.0:1.0, up to about 20.0:1.0, and preferably from about 3.0:1.0 up to about 15.0:1.0. A common practice entails utilizing a plurality of feed loci.

Alkylation reaction conditions include temperatures in the range of about 0° to about 200° F., and preferably from about 30° F. to about 110° F. In view of the fact that the alkylation reaction is highly exothermic, suitable means for removing heat from the reaction zone is generally provided. In general practice, the reaction zone is designed such that it functions as a form of heat-exchanger. Alkylation pressures are sufficiently high to maintain the hydrocarbons and hydrogen fluoride catalyst in substantially liquid phase; that is, from about 15 psig. to about 600 psig. The contact time in the alkylation reactor is most conveniently expressed in terms of a space-time relationship which is defined as the volume of catalyst within the reactor, or contacting zone, divided by the volume rate per minute of hydrocarbon reactants charged to the zone. Usually, the space-time relationship will be less than about 5 minutes and preferably less than about 2 minutes.

As is the common current practice, the product effluent from the alkylation reaction zone is introduced into a first separation zone generally comprising a two-vessel stacked system. The reaction mixture is introduced into the lower vessel which serves as a vertical mixer, or soaking zone. The mixer is sized and designed to provide an average residence time of the effluent mixture in the range of about 60 seconds to about 1200 seconds, depending upon the composition of the mixture charged to the mixer-settler. Turbulent-flow within the mixture is produced by internal means such as perforated plates or decks. After the desired residence time has been attained, the effluent is introduced into the upper vessel which serves as a settler to provide a hydrocarbon stream substantially free from the major portion of hydrogen fluoride and settled hydrogen fluoride which is substantially free from the major proportion of hydrocarbons. In a relatively recent technique, at least a portion of the reaction zone effluent is emulsified and recycled to the alkylation reaction zone. It is understood, however, that this prior art technique forms no essential part of the present inventive concept, or the alkylation process encompassed thereby. The settled hydrogen fluoride is recycled to the reaction zone in admixture with regenerated hydrogen fluoride as hereinafter set forth. The reaction zone effluent generally contains a relatively minor proportion of polymer products and other foreign matter which is formed during the alkylation reaction. These polymer products appear in the hydrogen fluoride phase removed from the lower portion of the settler. In order to prevent the build-up of polymer products within the reaction system, a relatively minor proportion of the settled hydrogen fluoride phase, containing polymer products, is introduced into an acid regenerator. In a typical prior art unit, processing approximately 10,000 Bbl./day of hydrocarbon reactant, the regenerator vessel is approximately 20 feet in length, and consists of approximately 14 feet of bubble cap trays and about 6 feet in the lower portion serving as a collection zone for the polymer products. In general, prior art processes utilize the acid regenerator on a periodic basis in view of the fact that improved operating techniques have resulted in a further decrease in the overall quantity of polymer products produced. On the basis of approximately 100 Bbl/day of hydrogen fluoride containing polymer products, the acid-regenerator will be employed in cycles approximately 7 to about 10 days, therefore processing about 700 to about 1000 barrels of hydrogen fluoride. The quantity of polymer products so recovered will range from about 5.0% to about 20.0% by volume of the total charge to the acid-regenerator. Recovered hydrogen fluoride is recycled to the alkylation reaction zone in admixture with the settled hydrogen fluoride. Such a periodic use of the acid-regenerator inherently leads to operational difficulties attendant upsets in the stable operation occurring each time the acid-regenerator is placed on-stream, and subsequently taken out of the system. In those units in which the periodic use of the acid-regenerator is not employed, but rather is on-stream continuously, an excessive amount of hydrogen fluoride, with respect to the quantity of polymer products, are necessarily introduced thereto. In accordance with the process of the present invention, the acid-regenerator is removed from the system.

The hydrocarbon phase separated in the settler vessel is introduced into an isostripper fractionating column for the recovery of the normally liquid alkylate product as a bottom stream. Propane, unreacted isobutane and hydrogen fluoride catalyst are removed as an overhead stream and introduced into a settling zone from which the hydrogen fluoride is recycled to the reaction zone. The hydrocarbon phase from this settler is introduced into a depropanizing column with isobutane being removed as a bottoms fraction and recycled in part to the reaction zone and in part to the acid-regenerator for the purpose of stripping hydrogen fluoride from the polymer products which are removed as a bottoms stream. A principally vaporous phase, predominantly propane and containing a minor quantity of hydrogen fluoride is introduced into a hydrogen fluoride stripping column. The hydrogen fluoride is removed as an overhead fraction and introduced into the isostripper settler for ultimate return to the reaction zone. Propane is normally removed from the bottom of the HF stripper and sent to storage. The propane-rich product stream is generally subjected to both alumina treating and potassium hydroxide treating to remove trace quantities of hydrogen fluoride. Similarly, although the normally liquid alkylate product is generally recovered substantially free from hydrogen fluoride, cautious operating techniques, as well as environmental considerations generally dictate that the same be subjected to similar treatments to remove trace quantities of hydrogen fluoride.

As hereinafter described in greater detail, upon reference to the accompanying drawings, the present invention involves the elimination of the acid-regenerator with the result that that portion of the settle hydrogen fluoride normally being introduced into the acid-regenerator is introduced directly into the isostripping column with the hydrocarbon phase from the settler. The temperature of these streams, as they emanate from the hydrogen fluoride settler, is generally in the range of about 80° F. to about 105° F. In accordance with the present invention, the temperature of only the hydrocarbon phase is increased to a level in the range of about 125° F. to about 200° F., to increase the solubility potential of hydrogen fluoride therein, prior to the introduction thereof into the isostripping column. That portion of the HF-acid phase, emanating from the settling zone, and not being recycled to the reaction zone, is not increased in temperature, but is commingled with the heated hydrocarbon phase and introduced therewith into the isostripping column. Noted should be the fact that this column is not refluxed—to do so would destroy completely the desired end object of recovering the alkylate bottoms product substantially free from hydrogen fluoride. The remainder of the process, being the isostripping column settler, the depropanizing column and the hydrogen fluoride stripper is much the same as that described with reference to a typical prior art alkylation process.

In further describing my invention, reference will be made to the accompanying drawings which are presented for the sole purpose of describing a typically prior art alkylation process as well as the improvement afforded through the utilization of the present invention. In the drawings, the process is presented by means of simplified flow diagrams in which such details as pumps, instrumentation and controls, quench systems, heat-exchange and heat-recovery circuits, valving, start-up lines and similar hardware have been eliminated as being non-essential to an understanding of the techniques involved. The use of such miscellaneous appurtenances, to modify the process as illustrated, will be evident to those possessing skill in the art of petroleum refining technology.

Briefly, FIG. 1 constitutes a simplified flow diagram of a typical present-day alkylation process which can be improved through the incorporation therein of the present inventive concept. Illustrated are the principle vessels reactor 4, mixer-soaker 11, hydrogen fluoride settler 13, acid-regenerator 15, isostripper 19, isostripper settler 25, depropanizer 27 and hydrogen fluoride stripper 29.

FIG. 2 constitutes an abbreviated simplified flow diagram illustrating the changes between the settler-mixer and isostripper 19 as a result of eliminating acid-regenerator 15 as shown in FIG. 1.

DESCRIPTION OF DRAWINGS

The drawings will be described in conjunction with a commercially-scaled unit designed for the alkylation of isobutane with a mixed olefin feed, containing propylene, butylene and amylene, in an exchanger-type reaction vessel. The olefinic hydrocarbon stream, in the amount of about 5,938 Bbl/day, enters the process via line 1; make-up isobutane is introduced via line 3; and, field butane, in the amount of about 1,000 Bbl/day is introduced into the system via line 20, the isobutane-rich portion thereof being recycled by way of line 2 to combine with the olefinic hydrocarbon and make-up isobutane mixture in line 1.

From these fresh feed charge streams, it is desired to produce a full boiling range, normally liquid alkylate product having a Reid vapor pressure of about 7.0 pounds; it is further intended to recover LPG grade (liquefied petroleum gas) propane, as well as a normal butane concentrate which is transported to storage.

Figure 1:
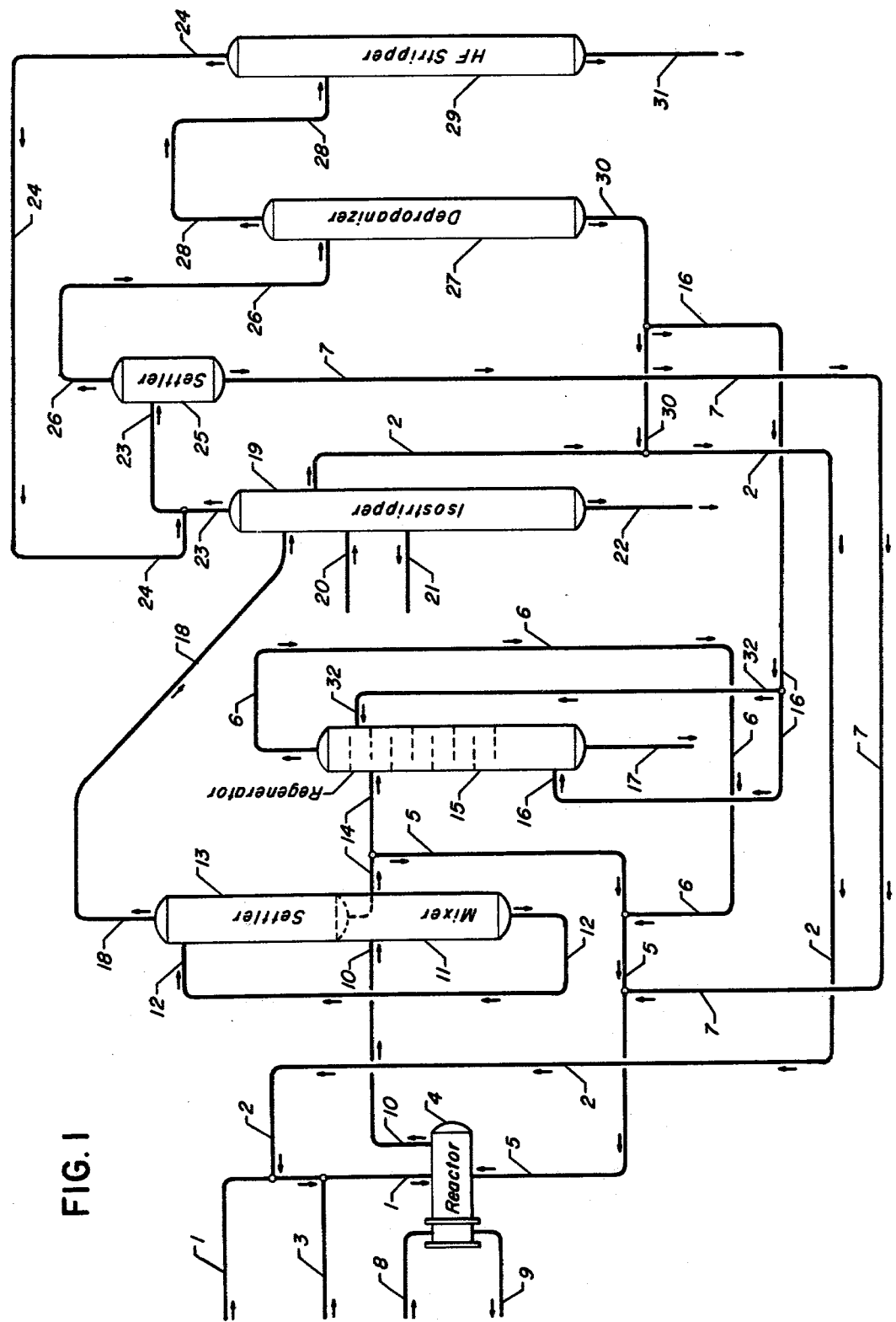

With specific reference now to FIG. 1, 5,938 Bbl/day of the olefinic feed stream (958.16 moles/hour), produced in a fluid catalytic cracking unit, is introduced into the process through line 1, and is admixed with 54,034 Bbl/day (7,699.74 moles/hour) of an isobutane-rich recycle stream in line 2, containing 116.09 moles of HF acid, and 2,657 Bbl/day (376.62 moles/hour) of make-up isobutane (95.0% by volume) from line 3, the mixture continuing through line 1 into alkylation reactor 4. The reactor is designed to function as a heat-exchanger having multiple feed injection points, which design is well known and not, therefore, illustrated herein. Hydrogen fluoride, in an amount of 95,724 Bbl/day (58,776.5 moles/hour), is recycled from settler 13 and introduced into reactor 4 by way of line 5. This stream is inclusive of 184.12 moles/hour of regenerated acid from line 6, also containing 322.08 moles/hour of an isobutane-rich stream, and 116.09 moles/hour of settled HF acid recovered in line 7 as hereinafter described. In reactor 4, the isobutane/olefinic hydrocarbon mole ratio is about 13.0:1.0 and the HF acid/hydrocarbon volumetric ratio is about 1.48:1.0. Reactor 4 is maintained at a pressure of about 233 psig., with the HF acid and reactant streams being introduced at a temperature of about 100° F. The material balance around reaction zone 4, exclusive of the HF acid stream, is presented in the following TABLE I, with the concentrations of the various components being given in terms of moles per hour for convenience.

TABLE I

| Reaction Zone Material Balance | | |
|---|---|---|
| Component | Charge | Effluent |
| Ethane | 1.00 | 1.00 |
| Propylene | 294.12 | — |
| Propane | 632.21 | 649.68 |
| Butylenes | 277.60 | — |
| Isobutane | 7471.23 | 6881.75 |
| N-Butane | 547.75 | 552.89 |
| Amylenes | 2.99 | — |
| Isopentane | 87.16 | 107.12 |
| N-Pentane | 0.64 | — |
| Hexane-plus | 41.00 | 586.77 |
| Polymer Products | — | 0.18 |

As hereinbefore set forth, HF alkylation of an isoparaffin/olefin reactant mixture is highly exothermic, and must be tempered through the use of a cooling medium. In the illustration, the heat of reaction is about 21.6×10⁶ BTU/hour, and is removed through the use of 8,685 gallons/minute of 85° F. water, entering via line 8, and exiting via line 9 at a temperature of about 90° F. The total reaction product effluent is withdrawn through line 10 at a temperature of about 100° F. and a pressure of about 218 psig.

The product effluent continues through line 10 into mixer/soaker 11, wherein it is maintained for an effective residence time of about eight minutes. After this holding period, the product effluent is transferred via line 12 into HF acid settler 13. Settled HF acid is removed via line 14 in the amount of 95,346 Bbl/day (58,544.30 moles/hour), at a pressure of about 203 psig. Of this amount, 95,046 Bbl/day (58,360 moles/hour) are diverted through line 5 as acid recycle to reactor 4. Generally, the remaining 300 Bbl/day (184.3 moles/hour) is accumulated until a sufficient quantity is available for introduction into acid regenerator 15. For the purpose of simplifying the present illustration, it will be presumed that the 184.3 moles/hour of HF (inclusive of polymer products) continues through line 14 into regenerator 15. Regenerator 15 functions at a bottom pressure of about 155 psig., a bottom temperature of about 350° F., a top pressure of about 145 psig. and a top temperature of about 160° F. HF acid is stripped from polymer products by the introduction, via line 16, of an isobutane-rich stream (229.90 moles/hour), at a temperature of 450° F. and pressure of 160 psig. Polymer products, in the amount of 3.5 Bbl/day (0.18 moles/hour) are recovered through line 17, at a pressure of about 155 psig. and a temperature of about 350° F. A portion of the isobutane-rich stripping stream from line 16 is diverted through line 32 in the amount of 92.18 moles/hour, cooled to a temperature of about 100° F., and introduced as reflux into acid regenerator 15. The overhead stream in line 6, comprising 322.08 moles/hour of hydrocarbons and 184.12 moles/hour of regenerated HF acid, is recycled to combine with the settled acid in line 5, and returned to reactor 4. The material balance with respect to acid regenerator 15 is presented in the following TABLE II:

TABLE II

| | Acid Regenerator Material Balance | | | | |
|---|---|---|---|---|---|
| | Line Number | | | | |
| Component | 14 | 32 | 16 | 6 | 17 |
| Ethane | — | — | — | — | — |
| Propylene | — | — | — | — | — |
| Propane | — | 1.08 | 7.00 | 8.08 | — |
| Butylenes | — | — | — | — | — |
| Isobutane | — | 85.22 | 215.39 | 300.61 | — |
| N-Butane | — | 5.32 | 6.99 | 12.31 | — |
| Amylenes | — | — | — | — | — |
| Isopentane | — | 0.56 | 0.52 | 1.08 | — |
| N-Pentane | — | — | — | — | — |
| Hexane-plus | — | — | — | — | — |
| HF Acid | 184.12 | — | — | 184.12 | — |
| Polymers | 0.18 | — | — | — | 0.18 |

The hydrocarbon-rich phase from settler 13, at a temperature of about 100° F. and a pressure of about 203 psig. is withdrawn through line 18, and consists of 8,779.21 moles/hour of hydrocarbons and 232.18 moles/hour of HF acid. This material is heated to a temperature of about 170° F., and introduced into isostripper 19 at a pressure of about 152 psig. Field butane, at a temperature of about 100° F., enters the upper section of isostripper 19 through line 20, in an amount of 144.16 moles/hour. A normal butane-rich stream, in the amount of 96.59 moles/hour, is recovered as a side-cut via line 21 and is subjected to treatment with potassium hydroxide for the removal of trace quantities of HF acid. Isostripper 19 functions at a bottom temperature of about 371° F., a bottom pressure of about 160 psig., a top temperature of about 140° F. and a top pressure of about 152 psig. The normally liquid alkylate product is recovered through line 22 in an amount of 6,426 Bbl/day (628.30 moles/hour), and is also subjected to caustic treating for acid removal. An isobutane-rich stream, in the amount of 4,472.22 moles/hour, including 21.28 moles/hour of a pump flush stream (not illustrated) from depropanizer 27 is recycled via lines 2 and 1 to reactor 4. Also recovered in line 2 is HF acid in the amount of 116.09 moles/hour. Overhead vapors, consisting of 1,495.08 moles/hour of hydrocarbons and 130.92 moles/hour of HF acid, is withdrawn through line 23. Of this amount, 747.54 moles/hour of hydrocarbons and 14.83 moles/hour of HF are used as reflux to isostripper 19; the composition of the hydrocarbon is 0.98 moles of isobutane, 26.99 moles of n-butane and 2.64 moles of isopentane. The component composition of the various charge and effluent streams, exclusive of HF acid, are presented in the following TABLES III and IV:

TABLE III

| Isostripper Feed Streams | | |
|---|---|---|
| Component | Line 18 | Line 20 |
| Ethane | 1.00 | — |
| Propylene | — | — |
| Propane | 649.68 | 3.36 |
| Butylenes | — | — |
| Isobutane | 6881.75 | 67.85 |
| N-Butane | 552.19 | 70.41 |
| Amylenes | — | — |
| Isopentane | 107.12 | 1.64 |
| N-Pentane | — | 0.90 |
| Hexane-plus | 586.77 | — |

TABLE IV

| Isostripper Effluent Streams | | | | |
|---|---|---|---|---|
| Component | Line 23 | Line 2 | Line 21 | Line 22 |
| Ethane | 1.98 | — | — | — |
| Propylene | — | — | — | — |
| Propane | 364.12 | 469.60 | — | — |
| Butylenes | — | — | — | — |
| Isobutane | 1070.07 | 6429.77 | 4.66 | 1.27 |
| N-Butane | 53.67 | 453.21 | 90.22 | 54.42 |
| Amylenes | — | — | — | — |
| Isopentane | 5.24 | 78.64 | 1.64 | 26.01 |
| N-Pentane | — | — | — | 0.90 |
| Hexane-plus | — | 41.00 | 0.07 | 545.70 |

A portion of the overhead from line 23 is diverted as reflux to the top of isostripper 19; this portion consists of 747.54 moles/hour of hydrocarbons and 14.83 moles/hour of HF. The remainder is admixed with 15.22 moles/hour of HF from line 24, and is introduced into settler 26.

Settled acid, in the amount of 116.09 moles/hour, is recycled to reactor 4 by way of lines 7 and 5. Hydrocarbons, in the amount of 761.70 moles/hour, and HF acid, in the amount of 15.22 moles/hour, are introduced via line 26 into depropanizer 27. A propane concentrate containing 15.22 moles/hour of HF acid is recovered as an overhead stream in line 28, being introduced thereby into HF stripper 29. The bottoms stream, 585.03 moles/hour is withdrawn through line 30 and utilized as follows: 35.47 moles/hour are employed as a pump flush stream (not illustrated); 322.08 moles/hour are diverted through line 16 for use in acid regenerator 15; and, 227.52 moles/hour continue through line 30 for recycle to reactor 4 via line 2. Depropanizer 27 functions with a bottom pressure of about 315 psig., a bottom temperature of about 220° F., a top temperature of about 140° F. and a top pressure of about 305 psig. The material balance for depropanizer 27 is presented in the following TABLE V:

TABLE V

| Depropanizer Material Balance | | | |
|---|---|---|---|
| Component | Line 26 | Line 28 | Line 30 |
| Ethane | 1.00 | 1.00 | — |
| Propane | 183.86 | 172.69 | 11.17 |
| Isobutane | 546.68 | 2.97 | 543.71 |
| N-Butane | 27.50 | — | 27.50 |
| Isopentane | 2.69 | — | 2.69 |

Hydrogen fluoride, in an amount of about 15.22 moles/hour is withdrawn as an overhead stream in line 24, and admixed with the isostripper overhead in line 23. The 176.66 moles/hour of hydrocarbons are recovered via line 31. HF stripper 29 functions with a top temperature of about 140° F., and a pressure of about 310 psig. and a bottoms temperature of 150° F., and a pressure of about 320 psig.

Figure 2:
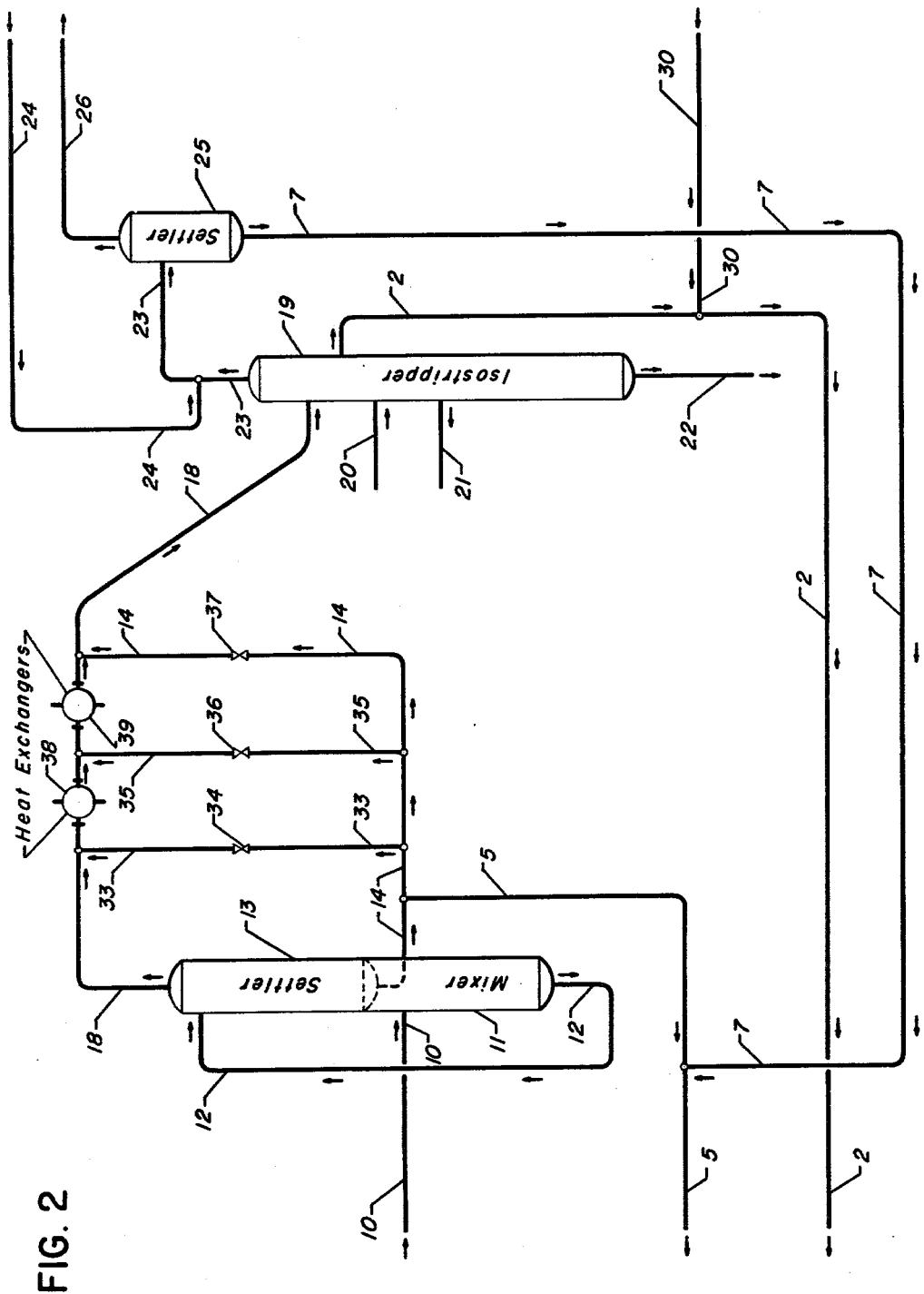

FIG. 2 indicates the changes resulting in the foregoing process through the use of the present invention. In the illustration, that portion of the process upstream of the settler/mixer and downstream of the isostripper and acid settler has been eliminated. The reaction product effluent is introduced via line 10 into mixer 11 and, after the effective residence time of eight minutes, is transferred through line 12 into settler 13. Settled acid is withdrawn through line 14, and the greater portion thereof is recycled back to the reaction zone via line 5. The 184.30 moles/hour of acid which otherwise would have been introduced into the acid regenerator, continues through line 14, containing valve 37, being admixed with the heated hydrocarbon-rich phase in line 18 just downstream from heat-exchanger 39. The temperature of the material entering isostripper 19 may be regulated through the use of the heat-exchange manifold consisting of line 33 containing valve 34 and line 35 containing valve 36, although this is not the preferred technique. Heat-exchangers 38 and 39 can utilize, as the heating medium, the hot effluent stream from the bottom of the isostripper, the hot effluent from the bottom of the depropanizer or both.

The streams withdrawn through lines 2, 21 and 23 have virtually the same composition as noted in the description of FIG. 1 with the exception of the additional HF acid. The polymer products are recovered through line 22 in admixture with the normally liquid alkylate product. Experience has proven that there is no product degradation stemming from the inclusion therein of these polymer products, as has been the popular belief heretofore.

As previously set forth, the net overhead from isostripper 19 is admixed with acid from the HF stripper in line 24, and continues through line 23 into acid settler 25. Line 26 transfers the hydrocarbon phase to the depropanizer, while line 7 carries the settled acid to the reaction vessel in admixture with the settled acid in line 5. Line 30, joining the isobutane-rich recycle stream in line 2, transfers the depropanizer bottoms product to the reaction vessel.

The normally liquid alkylate product withdrawn via line 22 has a Reid Vapor Pressure of 9.9 lbs., a clear octane rating of 93.3 (research method), 104.2 with 3.0 cc. of tetraethyl lead and a gravity of 74.6 °API. The results of a 100-ml. ASTM distillation is presented in the following TABLE VI:

The significant advantages attendant the elimination of the acid regenerator will be apparent to those having skill in the art of petroleum refining technology. It will be noted, for example, that lines 16, 6, 17 and 32 have also been eliminated as well as the various heat-exchangers, coolers, valves, controls, etc. which are otherwise appurtenant thereto.

TABLE VI

| Alkylate Product ASTM Distillation | |
|---|---|
| Volume Percent | °F. |
| Initial Boiling Point | 92 |
| 5.0% | 119 |

TABLE VI-continued

| Alkylate Product ASTM Distillation | |
|---|---|
| Volume Percent | °F. |
| 10.0% | 136 |
| 20.0% | 170 |
| 30.0% | 196 |
| 40.0% | 206 |
| 50.0% | 212 |
| 60.0% | 218 |
| 70.0% | 223 |
| 80.0% | 234 |
| 90.0% | 273 |
| 95.0% | — |
| End Boiling Point | 356 |

I claim as my invention:

1. A process for the alkylation of an isoparaffin with an olefin, to produce a normally liquid alkylate product, which process comprises the steps of:
   (a) reacting said isoparaffin with said olefin, in admixture with a hydrogen fluoride catalyst, in an alkylation reaction zone, at alkylating conditions resulting in a reaction product effluent containing (i) normally liquid alkylate, (ii) unreacted isoparaffin, (iii) hydrogen fluoride catalyst and, (iv) polymer products;
   (b) introducing said reaction product effluent into a separation zone and therein settling the same into (i) a liquid hydrocarbon phase and, (ii) a liquid hydrogen fluoride phase containing said polymer products;
   (c) recycling a first portion of said liquid hydrogen fluoride phase to said reaction zone for contact therein with said isoparaffin and olefin;
   (d) heating said liquid hydrocarbon phase to a tempeerature greater than the temperature of said reaction product effluent, and in the range of about 125° F. to about 200° F.;
   (e) commingling a second unheated portion of said liquid hydrogen fluoride phase with said heated hydrocarbon phase, in an amount which is soluble in said heated hydrocarbon phase; and,
   (f) stripping the resulting mixture, in a stripping zone, in countercurrent contact with an isoparaffin-containing stream and separately removing therefrom (i) unreacted isoparaffin with residual hydrogen fluoride and, (ii) said normally liquid alkylate product, containing polymer products.

2. The process of claim 1 further characterized in that said isoparaffin contains from about four to about seven carbon atoms per molecule.

3. The process of claim 1 further characterized in that said olefin contains from about three to about seven carbon atoms per molecule.

4. The process of claim 2 further characterized in that said isoparaffin is isobutane.

5. The process of claim 3 further characterized in that said olefin is propylene.

6. The process of claim 3 further characterized in that said olefin is a butylene.

7. The process of claim 3 further characterized in that said olefin is a mixture of propylene and butylene.

8. The process of claim 1 further characterized in that said alkylating conditions include an isoparaffin/olefin molar ratio in the range of about 1.1:1.0 to about 20.0:1.0 and a temperature from about 0° F. to about 200° F.

* * * * *